(12) United States Patent
Vasala et al.

(10) Patent No.: US 9,228,167 B2
(45) Date of Patent: Jan. 5, 2016

(54) METHOD FOR CONTROLLING THE GROWTH OF CELL CULTURE

(75) Inventors: Antti Vasala, Oulu (FI); Peter Neubauer, Oulu (FI); Johanna Panula-Perala, Oulu (FI)

(73) Assignee: OULUN YLIOPISTO, Oulun Yliopisto (FI)

( * ) Notice: Subject to any disclaimer, the term of this patent is extended or adjusted under 35 U.S.C. 154(b) by 739 days.

(21) Appl. No.: 12/517,151

(22) PCT Filed: Nov. 29, 2007

(86) PCT No.: PCT/FI2007/050648
§ 371 (c)(1),
(2), (4) Date: Jun. 1, 2009

(87) PCT Pub. No.: WO2008/065254
PCT Pub. Date: Jun. 5, 2008

(65) Prior Publication Data
US 2010/0099164 A1    Apr. 22, 2010

(30) Foreign Application Priority Data

Nov. 30, 2006  (FI) ..................................... 20065762

(51) Int. Cl.
*C12N 1/22* (2006.01)
(52) U.S. Cl.
CPC ...................................... *C12N 1/22* (2013.01)
(58) Field of Classification Search
None
See application file for complete search history.

(56) References Cited

U.S. PATENT DOCUMENTS

| 3,926,723 A | 12/1975 | Green et al. |
| 2004/0161842 A1 | 8/2004 | Daugulis et al. |
| 2005/0176120 A1* | 8/2005 | Otto .............................. 435/139 |
| 2007/0207238 A1* | 9/2007 | Sugimoto et al. ............... 426/46 |
| 2009/0104655 A1 | 4/2009 | Buchs et al. |

FOREIGN PATENT DOCUMENTS

| JP | WO/2005/097967 | * 10/2005 | .............. C12G 3/02 |
| WO | 2006/119867 | 11/2006 | |

OTHER PUBLICATIONS

Hofsten et al. (Degradation of Agar by a Gram-negative Bacterium., Journal of General Microbiology, 1975, vol. 87, pp. 150-158.*
The Seed Biology Place (last viewed on Jun. 13, 2012).*
Negi et al., Optimization of Amylase and Protease Production from Aspergillus awamori in Single Bioreactor Through EVOP Factorial Design Technique., Food Technol. Biotechnol., 2006, vol. 44(2), pp. 257-261.*
BD Bionutrients Technicla Manual (Oct. 2006).*

(Continued)

*Primary Examiner* — Alexander Kim
(74) *Attorney, Agent, or Firm* — Young & Thompson (57) ABSTRACT

In a method for controlling the growth of microbes grown in a medium to high cell-densities by the fed-batch technology, a two-phase system, having a liquid phase (cultivation medium) and a solid or gel phase, the solid or gel phase provides a source of substrate-delivering polymer which is turned by an enzyme in a controlled way into a growth-limiting substrate or pH adjusting agent. Also described is a method for restricting the synthesis of growth-limiting metabolites and preventing oxygen-depletion in microbial cell cultures.

19 Claims, 5 Drawing Sheets (56) References Cited

OTHER PUBLICATIONS

Brnzel, Herbert Horace (1910), A dissertation for PhD, University of Chicago, The Mechanism of the oxidation of glucose by bromine, p. 157 only.*
Hofvendahl et al., Factors affecting the fermentative lactic acid production from renewable resources., Enzyme and Microbial Technology (2000), vol. 26, pp. 87-107.*
Liu et al., Release of theophylline from polymer blend hydrogels., International Journal of Pharmaceutics (2005), vol. 298, pp. 117-125.*
Asenjo J A et al: "0ptimization of Batch Processes Involving Simultaneous Enzymatic and Microbial Reactions", Biotechnology and Bioengineering, Jan. 1, 1991, pp. 1087-1094, ,vol. 37, No. 11, Wiley & Sons, Hoboken, NJ, US ,DOI: 10.1002/BIT.260371114, XP002538162.
European Search Report, Dated Oct. 13, 2010, in Application No. EP 07 84 8180.
J. N. Dholakia et al, "Fermentative Production of B-Carotene and Extracellular B-Glucosidase by Blakeslea trispora Grown on Cellobise", European Journal of Applied Microbiology and Biotechnology, 1982, vol. 15, p. 33-35.
Elizabeth A. Tyrrell et al., "Biphasic system for growing bacteria in concentrated culture", Journal of Bacteriology, 1958, vol. 75, No. 1, pp. 1-4.
Andreas Seiffert et al., "Production of the Siderophore Enterobactin: Use of Four Different Fermentation Systems and Identification of the Compound by HPLC", Biotechnology and Bioengineering, 1993, vol. 41, No. 2, pp. 234-244.
M. Jeude et al., "Fed-Batch Mode in Shake Flasks by Slow-Release Technique", Biotechnology and Bioengineering, 1993, vol. 95, No. 3, pp. 433-445.
BioClub 10.10.2006: Dr Simon Curvers, AC Biotec GmbH: "Fed-batch in shaken bioreactors: a novel technique to improve screening success", URL: http://www.life-tec.org/Hauptseiten/events-archiv-bioclub-Curvers.htm, http://www.acbiotec.com/english/5_feedbeads.htm.
C. Lubbe et al., "Use of controlled-released polymer to feed ammonium to Streptomyces clavuligerus cephalosporin fermentations in shake flask", Applied and Microbiology Biotechnology, 1985, vol. 22, pp. 424-427.
Panula Johanna, "Integrated continuous glucose delivery system for fed-batch cultivation in shake flask", Master's thesis, University of Oulu, Department of Process and Environmental Engineering, Bioprocess Engineering Laboratory. p. 1.
Saurabh Gupta et al., "Improved xylanase production from a haloalkalophilic *Staphylococcus* sp. SG-13 using inexpensive agricultural residues", World Journal of Microbiology & Biotechnology, 2001, vol. 17, p. 5-8.
Sandeep Kaur et al., "Enhanced production and characterization of a highly thermostable alkaline protease from *Bacillus* sp. P-2", World Journal of Microbiology & Biotechnology, 2001, vol. 17, pp. 125-129.
Johanna Panula-Perala et al., "Controlled high-cell density cultivation in shake flasks", Journal of Biotechnology, Sep. 2007, vol. 131, Issue 2, Supplement 1, p. S182.
International Search Report dated Apr. 8, 2008, from corresponding PCT application.
Finnish Search Report dated May 24, 2007, from corresponding Finnish application.
Master's Thesis, University of Oulu, Department of Process and Environmental Engineering, Bioprocess Engineering Laboratory, Nov. 2006, XP008 14502.
European Office Action, dated Nov. 23, 2011, in Application No. 07848180.1.

* cited by examiner

METHOD FOR CONTROLLING THE GROWTH OF CELL CULTURE

FIELD OF THE INVENTION

The present invention relates to the field of high-cell-density cultivation. More particularly the present invention relates to a method for controlling the growth of microbes grown in a medium to high-cell-densities by the fed-batch technology.

BACKGROUND OF THE INVENTION

Shaken cultures are usually batch-cultures where all the components are added at the beginning of the cultivation. Too high substrate concentration, inadequate aeration, uncontrolled growth, synthesis of harmful metabolites (over-flow or anaerobic metabolisms), catabolite repression, and even substrate intoxication easily emerge in non-controlled shaken cultures. The biomass yield in shaken *E. coli* cultures is typically in the range of 1-2 g/l (dry weight), in microscale often much lower. With well-designed substrate feeding and pH control up to 50-fold higher biomass can be produced in commonly used conventional laboratories or industrial bioreactors. Control strategies (continuous monitoring and controlling) as applied in larger scale are not easily applicable in small shaken cultures. Setup of continuous monitoring and feeding is difficult to realize in the small scale. Non-controlled growth and insufficient aeration will fast bring oxygen-depletion. During oxygen limitation fermentation products (acetate, $CO_2$, formic acid, lactic acid, ethanol, succinic acid) are formed in quantities which inhibit the growth of bacteria and impair recombinant protein processes. Some of these metabolites can be synthesized also under aerobic conditions, if glucose uptake and glycolysis are faster than the capacity of the citric acid cycle. During such over-flow metabolism acetyl-CoA is transformed into acetate which is secreted to the culture medium. Catabolic repression of respiration (Crabtree effect) can occur also during long-term exposure to high glucose concentrations even in aerobic conditions.

To avoid oxygen limitation, over-flow metabolism and the Crabtree effect, high-cell-density cultivations in bioreactors normally apply the fed-batch technology. In substrate-limited fed-batch cultivation the bacterial growth rate can be controlled with one limiting substrate (typically glucose which is used as the sole carbon source). Oxygen consumption increases relative to respiratory activity (substrate usage) and growth rate. Therefore, by suppressing growth of microbes by substrate-limitation also oxygen limitation can be avoided. However the majority of simple cultivations are done in shake flasks without monitoring or feeding possibilities. The applied cultivation method is usually batch-cultivation. The biomass yield typically remains low, and the quality of the so-produced culture is non-predictable and often poor. High-cell-densities are not achieved with the batch method because such cell densities would require so high initial consentration of nutrients that it would be toxic to the microbe.

Since measuring and feeding devices are not normally applicable for simple shaken cultures, alternative strategies have been developed. In medical therapies drugs are often supplied by slow release of a substrate over a long period of time. Drug delivery-like systems are rarely applied in microbial cultivations, as the substrates normally are small molecules such as glucose and ammonia, for which the release rate is difficult to control. With a "drug-delivery" like system Lübbe et al. (Appl Microbiol Biotechnol (1985) 22: 424-427) have supplied $NH_4Cl$ in *Streptomyces clavuligerus* cultivation and recently Jeude et al. (Biotechnol Bioeng (2006) Vol. 96, No. 3:433-443) have used silicone elastomer (polydimethylsiloxane) disks containing glucose to create fed-batch like conditions for cultivations (see also Büchs et al. WO 2006/119867 "Fermentation method and apparatus for its implementation") These disks can be added to cultivation vessels, but they are not integrated parts of them. However, relatively small amounts of glucose can be packed into such a matrix. Furthermore, the glucose release rate from such matrix is usually fastest in the beginning of cultivation, when the amount of microorganisms is lowest and the risk for over-flow metabolism is highest. This may explain, why such systems have not rapidly become popular in simple cultivations of the biotechnologically most important bacterial species, *Escherichia coli*.

Tyrell et al. (J. Bacteriol 75 (1958): 1-4; "Biphasic system for growing bacteria in concentrated culture") have presented a method to pack nutrients like yeast extract into a gel. This method however has no possibilities of controlling the release rate of nutrients, especially glucose-release from such a gel occurs extremely fast. Therefore it is not applicable for high-cell-density cultivation. This method never became popular, since nutrient-rich well-buffered complex cultivation media like super broth or terrific broth are easier to use and provide higher cell densities.

An interesting application for animal cell cultures has been presented by Green and James (U.S. Pat. No. 3,926,723 "Method of controllably releasing glucose to a cell culture medium" 1975). They used small amount of soluble starch as the carbon source for cells. The horse, pig or bovine serum used in cultivation medium provided enough catalytic activity to release gradually small amounts of glucose. Also added enzymes could be used instead of the serum enzymes. This approach used only 2 g/l of starch, which in theory would support max 1 g/l of biomass (cells). In human cell cultures no significant increase of cell number was obtained. It was not used for controlling or limiting culture growth rate, but instead it was only used to prevent accumulation of one growth-retarding compound, lactic acid. Thus the authors seem not to be aware of the fed-batch technology as a strategy for reaching high cell densities and with the low concentration of starch they used their method can not be regarded as a high-cell-density cultivation. For bacterial cultivations (e.g. for *Escherichia coli*) this approach will not work: complex cultivation media such as serum, yeast extract or peptones contain several components which can function as a carbon-source. Therefore growth control can not be obtained by limiting the concentration of one carbon source (e.g. glucose). In microbial fed-batch cultivations, chemically defined media and only one growth-limiting substrate are typically used at a time. Furthermore, as will be shown in accordance of the present invention, only small amounts of starch can remain soluble in the medium to provide enough glucose for high-cell-density microbial cultivations. For aerobically growing microbes the presence of high amounts of starch severely weakens the oxygen transfer capacity of the medium and thereby increases the risks of anaerobic metabolism. For this reason, an intelligent system to pack high amount of carbon source into culture vessels is required.

The slow-release approaches so far published are limited in 1) scalability, 2) the amount of the delivered substrate that can be packed to the system or 3) methods to accurately control the substrate-release. None of the above-described methods provide an integrated solution for all of these essential requirements for high-cell-density cultivation of microbes in simple shaken cultures. In methods based on enzymatic degradation of a substrate delivering polymer, high amounts of polymer must be loaded to the cultivation vessel without impairing the properties (e.g. oxygen transfer capacity) of the cultivation medium.

SUMMARY OF THE INVENTION

In the present invention an advantageous controlled slow substrate release was obtained surprisingly by enzymatic digestion of a polymer immobilized into a gel on the bottom of a shaken bioreactor without computer aided control or external feeding devices. A two-phase system was developed in order to allow 1) packing of high amount of carbon source that is not directly digestible by the cells that will be grown to support high cell densities and 2) retarded release of the said non-digestible carbon source to a liquid phase. As an example, glucoamylase-catalyzed release of glucose from starch is presented. Oxygen-limitation could be avoided and higher biomass obtained in E. coli cultivations in shake flasks and deep-well plates. Small amount of glucose in the medium (prior to addition of glucoamylase) can be used in order to fast obtain enough bacteria to immediately consume the released glucose. With the optimized protocol, significantly higher cell densities can be used for induction of recombinant genes' expression, and consequently higher product yields can be obtained.

The present invention provides a method for controlling the growth of microbes grown in a medium to high cell-densities by the fed-batch technology wherein in a two-phase system, having a liquid phase (cultivation medium) and a solid or gel phase, the solid or gel phase provides a source of substrate-delivering polymer which is turned by an enzyme in a controlled way into a growth-limiting substrate or pH adjusting agent. By the use of the solid or gel phase, the substrate-delivering polymer can be packed to the system in amounts that support high cell-densities without impairing the physical properties of the liquid phase.

The present invention applies the fed-batch method to non-controlled shaken microbial cultures in order to reach high cell densities (i.e. considerably higher than the cell densities obtained by batch-cultivations) without external feeding. The growth-limiting substrate (e.g. glucose) is obtained by enzymatic release from a polymer (e.g. starch) which is integrated or immobilized to a gel. The use of a two-phase system allows the packing of high amounts of polymer into the culture vessel so that it can be slowly released from the solid or gel phase into the liquid phase without impairing the physical properties (e.g. oxygen transfer properties) of the liquid. The polymer is not immediately available and the substrate will be released by the enzyme in a controlled way to obtain a desired release rate. Also the total amount of the growth-limiting substrate released into the medium can be tailored. An optimized controlled substrate-release rate can be obtained e.g. simply by controlling the gel composition, controlling (i.e. varying) the enzyme concentration or controlling (i.e. varying) the enzyme activity, e.g. by enzyme modification. Such system is scaleable and applicable for various bioreactor systems.

An advantage of the method of the present invention is that the synthesis of growth-limiting metabolites in the cell culture can be restricted. This is obtained by preventing excessive substrate feed (the cause of over-flow metabolisms) and non-controlled growth (the cause of oxygen depletion). The method of the invention is also useful for controlling the pH of the cell culture. Another advantage is that pumps or other external devices are not required and therefore the cultivation system can be simple and cost-efficient.

One aspect of the present invention provides a method for controlling the growth of an organism cultivated in a medium, wherein a growth-limiting substrate is released in a controlled way from a substrate-delivering polymer into the medium by enzymatic action. Said growth-limiting substrate may be e.g. a nutrient or a pH adjusting agent.

Another aspect of the present invention provides a method for restricting the synthesis of growth-limiting metabolites in a cell culture, wherein said method for controlling the growth is used to release a growth-limiting substrate slowly to the cells to restrict the synthesis of growth-limiting metabolites.

Still another aspect of the present invention provides a method for preventing oxygen limitation (or depletion as the words may be used interchangeably) in a cell culture by utilizing the above-mentioned methods.

Still another aspect of the present invention provides a method for controlling pH of a cell culture wherein a pH adjusting agent is released in a controlled way from a polymer into the medium by enzymatic action of a polymer-degrading enzyme.

Still another aspect of the present invention provides the use of gel-like material capable of releasing a growth-limiting substrate in a controlled way from a polymer into a cell cultivation medium by enzymatic action of a polymer-degrading enzyme for controlling the growth of an organism cultivated in the medium by the methods of the invention.

Still another aspect of the present invention provides a high-cell-density fed-batch technology-based cultivation system for controlling the growth of microbes cultivated in a medium by the methods of the invention.

Still another aspect of the present invention provides a high cell-density fed-batch technology-based cultivation kit for controlling the growth of microbes cultivated in a medium by the methods of the invention.

BRIEF DESCRIPTION OF THE DRAWINGS

FIG. 1 shows the principle of how the method of the invention can be applied. Substrate delivery is based on a two-phase system comprising a liquid cultivation medium and a substrate delivering gel. The growth-limiting substrate is derived from a polymer which is bound to the gel. The polymer is gradually released to the medium, where a specific enzyme releases the substrate from A) a simple gel, B) a two-gel system where an overlaid gel retards the release of polymer, C) a system where the microorganism itself produces the substrate-digesting enzyme. In FIG. 1 said gel or a two-gel system is in the form of a bottom plate.

DETAILED DESCRIPTION OF THE INVENTION

The present invention provides a method for controlling the growth of microbes grown in a medium to high cell-densities by the fed-batch technology.

As used herein "high-cell-density cultivation" refers to a cultivation which yields high number of microbial cells. This requires a high amount of nutrients. To avoid inhibitory or toxic effects of high nutrient concentration, strategies like continuous flushing of nutrients and metabolites in membrane bioreactor or slow substrate feeding (fed-batch) must generally be applied. High cell-density value is dependent on the microbe. It can be defined as the cell density that would not be reached without gradual addition of nutrients (fed-batch) without toxicating the microbe.

As used herein "batch cultivation" refers to a cultivation process, where all components are added in the beginning of cultivation. No external feeding occurs during cultivation. As used herein "fed-batch" refers to a cultivation, where nutrients are gradually fed during the cultivation. As used herein "substrate-limited fed-batch" refers to a cultivation method, where the growth of microbes is controlled with one limiting nutrient, for example by the use of glucose as the only carbon source.

The present invention comprises a two-phase system having a liquid phase and a solid or gel phase.

The "liquid phase" as used herein refers to any suitable liquid phase capable of acting as the cultivating medium. Examples of the liquid phase include derivatives of commonly used chemically defined media (also known as mineral salt media). Such media can be easily modified by omitting one or more components (e.g. chemicals that are carbon-sources for the cultivated organisms) thus providing basis for controlled substrate-limited fed-batch by the method of invention. Generally the liquid phase contains the cells and the enzyme(s).

The "solid phase" refers to any suitable solid phase capable of providing the source of substrate-delivering polymer. One embodiment of the solid phase is a gel or a gel-like matrix. The "gel-like matrix" as used herein refers to any suitable gel or gel-like matrix useful in accordance with the present invention, such as agar-gels, carrageen-gels or gelatin-gels. Non-limiting examples of suitable solid phases include also any substrates-delivering polymers that are not freely dispersed to the liquid phase. In one embodiment there is a further second gel on the first solid or gel phase to retard the release of the growth-limiting substrate (two-gel system). The second gel may be e.g. a top gel on a bottom plate or a layer on a bead.

Said solid phase provides a source of substrate-delivering polymer. In one embodiment the substrate-delivering polymer is integrated or immobilized in a gel-like matrix. This can be achieved by adding the substrate-delivering polymer into water or medium which contains a gel-forming compound like agar. Heating of such liquid dissolves the gel-forming compound, which after cooling entraps the substrate-delivering polymer into the gel matrix. Gel can be formed also by compounds which are polymerazed by action of other chemicals or light. In such cases the matrix may not be degraded by the enzymatic action described but it only serves as a stabilizer or support. The substrate-delivering polymer may be degraded by the enzyme either directly on or in the matrix, wherein the enzyme is able to degrade the polymer or it is able to penetrate into the matrix, or the substrate-delivering polymer is degraded by the enzyme after release into the medium from the matrix by diffusion. In one embodiment after addition of the liquid part the substrate-delivering polymer starts to disperse into the liquid phase. In one embodiment the substrate-delivering polymer cannot be directly used by the microbe.

Suitable polymers capable of acting as substrate-delivering polymer to the enzyme include several types of polymers. In one embodiment the polymer is a polysaccharide, such as starch, agar, carrageen, glycogen or peptidoglycans or the like. One specific example of polysaccharide polymer is starch which can be digested by glucoamylase enzyme to produce glucose. In another embodiment the polymer is a protein or a polypeptide, such as collagen, gelatine or the like, and the amino acids or peptides are released enzymatically. In still another embodiment the polymer is a phosphate-containing compound, such as nucleic acid, polyphosphate or the like. In still another embodiment the polymer is a nitrogen-containing compound, such as polyacrylamide or polyamine or protein.

Suitable enzymes for use in the methods of the present invention include all the enzymes known in the art capable of digesting the polymer used to provide nutrients to the cells or a pH adjusting agent. Non-limiting examples of such enzymes include amylases and glucoamylases for starch and proteases, peptidases and amidases for proteins, polypeptides and compounds rich in amino groups. Further non-limiting examples illustrating the application potential are the degradation of nucleic acids by nucleases, the use of amidases to release ammonium groups from a polymer, or lipases for the degradation of lipids. The enzyme may be added to the medium or it may be produced by the microorganism. In the latter case it may be a wild-type enzyme naturally produced by the organism or it may be a recombinant enzyme. The amount of added enzyme or the level of the enzyme produced by the organism can be used to control the release of the nutrient from the polymer. As a distinction to the naturally occurring digestion of polymers (like starch) directly suspended into the medium with microbe-produced enzymes, the present invention provides a two-phase system which can provide substrate-feed for high cell densities without impairing the physical properties of the cultivation medium. To provide optimal conditions for the specific application also a cocktail of enzymes can be used and several polymers can be together applied in one and the same cultivation.

Figure 2A:
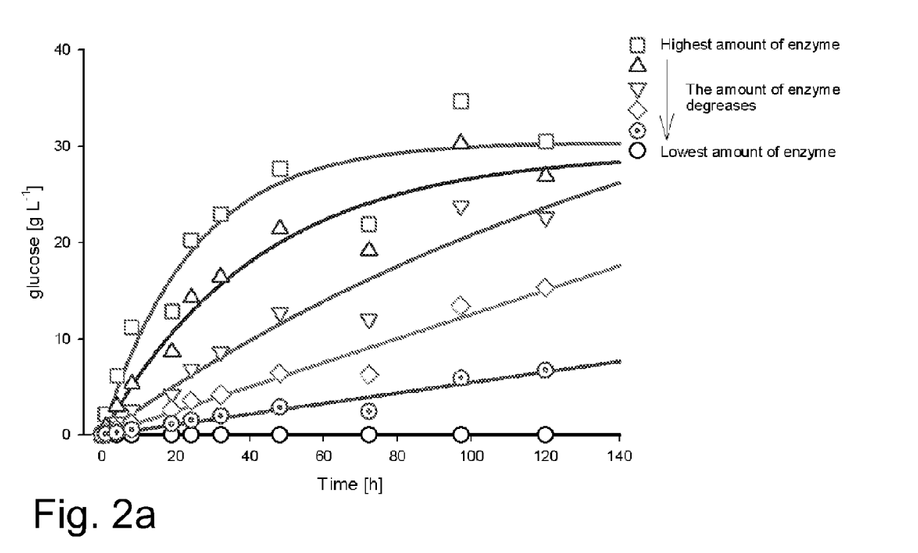
FIG. 2 shows that a desired release rate of glucose from starch can be obtained by optimizing the concentration of glucoamylase enzyme which removes single glucose molecules from starch (A). The release of starch from gel to the medium can be retarded by casting a thin layer of agar (top-gel) on top of the starch-agar gel (B).
Figure 2B:
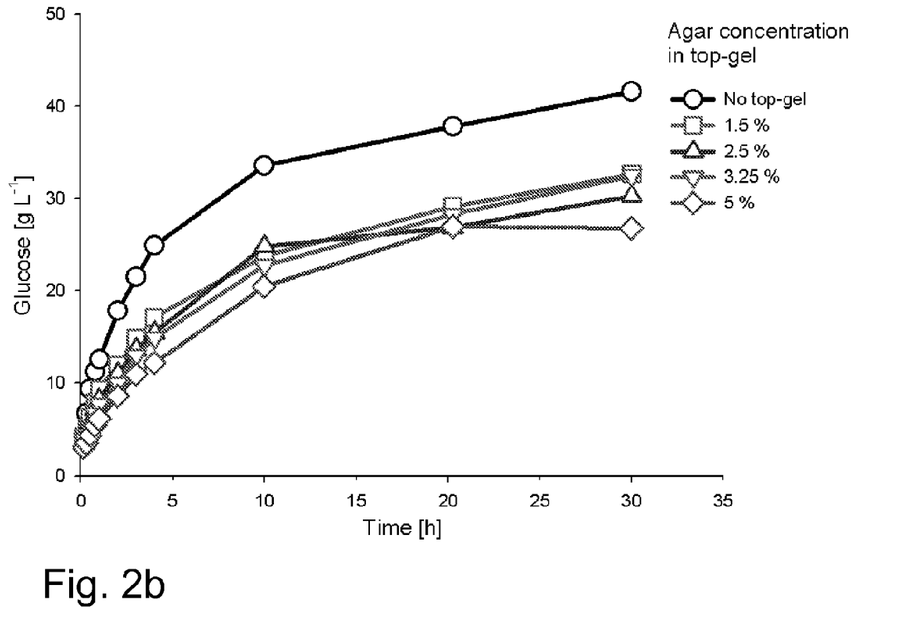

To control the growth of the microbes the substrate-delivering polymer is turned by an enzyme into a growth-limiting substrate or pH adjusting agent. To provide substrate-limiting conditions, the activity or the amount of the used enzyme can be controlled (FIG. 2).

The "growth-limiting substrate" as used herein refers to any suitable substance which affects the cultivated organisms' capability to grow. In one embodiment the growth-limiting substrate is a nutrient, such as a major nutrient, for example glucose. In another embodiment the growth-limiting substrate is a pH adjusting agent, such as ammonia, which affects the pH of the cultivation medium, therefore controlling the growth not exclusively based on its availability but also by controlling the environment (pH) thus affecting the growth rate of the cells. It may be advantageous to use only one type of growth-limiting substrate to obtain better controllability of the cell growth.

Growth-limiting substrate source, i.e. a polymer capable of releasing the substrate, may be immobilized or integrated to the solid or the gel phase. This provides a two-phase system comprising a liquid cultivation medium and the substrate reservoir gel. Immobilization or integration can be based on the gel-forming properties of the substrate source or on the use of other gel-forming substances (e.g., agar, carrageen, gelatine, collagen). With the use of the substrate-providing gel instead of directly suspending the polymer into the liquid phase, sufficient amounts of substrate for high-cell-density cultivation can be provided without the risk of heavily increasing the viscosity or impairing the oxygen transfer rate of the cultivation medium.

Figure 1:
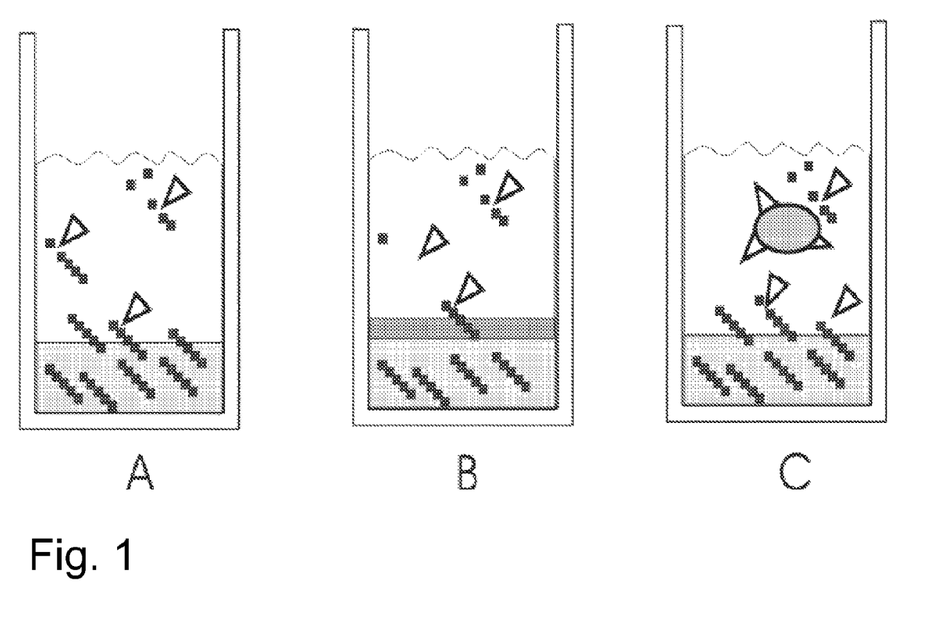

The feed of the growth-limiting substrate may be obtained by enzymatic digestion of a polymer (or substrate polymer) which is immobilized to a gel (FIG. 1) where it is gradually released to medium, where a specific enzyme degrades the polymer to create a substrate which can be used by the cells. The release rate of the substrate can be tightly controlled by enzyme dosing, which provides much better control of the substrate release compared to the system based on glucose release from silico-elastomer matrix system. In one embodiment the polymer is bound to a simple gel (FIG. 1A). In another embodiment the polymer is bound to a two-gel system where an overlaid gel retards the release of polymer (FIG. 1B). In still another one embodiment the polymer is released to medium, where the microorganism itself produces the digestive enzyme. In one embodiment the gel or the gel-like matrix is in the form of a bottom plate. In another embodiment the gel or the gel-like matrix is in the form of beads, which are capable of swimming in the solution. Such beads are well-known in the art and the size thereof may be e.g. in the range of 0.5-10 mm. Generally beads of this size are used for immobilization of microorganisms in agar or carragenan gels.

The principle of enzyme-based delivery method can be applied also to supplying nitrogen and to elevating the pH. A polymeric chemical which supplies nitrogen can be digested by an appropriate enzyme. Examples of such system include 1) polyacrylamide or corresponding chemical from which amino groups can be enzymatically released for example by amidase enzyme and 2) gel-forming proteins (e.g. gelatine) which is gradually digested by proteases, peptidases or amidases. Release of ammonia from such compounds can elevate pH and facilitate control of pH in simple cultivations.

The methods of the present invention may be controlled by optimizing several parameters, such as the gel composition, enzyme concentration, enzymatic activity, or by inoculating with such high amount of microbes which will immediately consume the released substrate or performing a batch cultivation in the presence of low amount of limiting substrate before addition of the enzyme.

The method of the invention is scalable over a wide range of volumes and can be applied on several different cultivation equipment and volumes. For example, the cultivation vessel may be a simple shaken bioreactor or a fermenter. The cultivation volume may be in the range of 1-1000 liters, such as a laboratory fermenter, in the range of 1 to over 100 $m^3$, such as industrial production reactors, in the range of 10 ml to 5 l, such as a shake flask, in the range of 1-10 ml, such as a cuvette, glass vial, falcon tube or the like, or in the range of 5 µl to 1 ml, such as a microtiter plate, minibioreactor or the like.

The present invention also provides a method for restricting the synthesis of growth-limiting metabolites in a microbial culture grown in a medium to high-cell-densities by the fed-batch technology wherein the method of the invention is used to release the growth-limiting substrate to the cells to restrict the synthesis of growth-limiting metabolites.

The present invention also provides a method for preventing oxygen limitation in a microbial cell culture grown to high-cell-densities wherein the method of the invention is used to release the growth-limiting substrate slowly to the cells to restrict the oxygen consumption.

The present invention also provides the use of gel-like material capable of releasing a substrate-delivering polymer into the microbial cell cultivation medium in the method of the invention.

The present invention also provides a high-cell-density fed-batch technology-based cultivation system for controlling the growth of microbes cultivated in a medium comprising a two-phase system having a liquid phase (cultivation medium) and a solid or gel phase, which provides a substrate-delivering polymer which is arranged to be turned in a controlled way by an enzyme to a growth-limiting substrate.

The present invention also provides a high-cell-density fed-batch technology cultivation kit for controlling the growth of microbes cultivated in a medium comprising a two-phase system having a liquid phase (cultivation medium) and a solid or gel phase, which provides a substrate-delivering polymer which is arranged to be turned in a controlled way by an enzyme to a growth-limiting substrate. The kit may also contain the appropriate enzyme(s) and any suitable bottles, vials, tubes, containers, microtiter plates or the like required and also printed instructions of how to use it.

As an non-limiting example, digestion of starch with glucoamylase is described. Soluble starch is immobilized onto the bottom of a shake flask or other simple bioreactor. The setup of a two-phase systems enables packaging of enough polymer for high-cell-density cultures. It also retards the release of the polymer into the liquid phase so that oxygen transfer potential of the medium is not immediately destroyed. Although starch can form stable gels, agar can be added to strengthen the gel and to control the release rate of starch to the cultivation medium. The polymer can not be immediately used as a carbon source by the microbes which lack polymer-degrading enzymes. With accurate dosing of an polymer-degrading enzyme, a defined release rate of a growth-limiting substrate can be achieved. With different amount of enzyme and with modifications to the gel composition, substrate (e.g. glucose) release rate can be controlled.

EXAMPLES

Example of a workable preparation method to immobilize starch to a gel is: starch (5 to 10% w/v) and agar (5 to 7% w/v) are mixed with cultivation medium or water. The mixture is sterilized in an autoclave, cooled to 60° C., shaken and then fast cooled in cold water to obtain a homogenous gel structure. After solidifying, cultivation medium (typically mineral salt medium without glucose or with low glucose content) and microbes are added.

FIG. 1 shows the principles how the method of invention can be applied. The growth-limiting substrate is derived from a polymer. The polymer is immobilized into a gel matrix which is fully or partly composed of the said polymer. The polymer is gradually released into the cultivation medium, where an appropriate enzyme (added manually) releases the growth-limiting nutrient from the polymer. To retard the polymer release rate, an extra gel can be laid over the polymer gel (FIG. 1B). To further limit the availability of the growth-limiting nutrient, enzyme dosing can be adjusted. FIG. 1C demonstrates the case where the polymer-degrading enzyme is encoded by the microorganism. The enzyme can be either a native or recombinant product of the microorganism. An example of such a system is the use of starch, which is digested with glucoamylase (E.C. 3.2.1.3.) enzyme.

As seen in FIG. 2, controlled release of glucose can be obtained by enzymatic digestion of glucose from starch with glucoamylase enzyme. By adjusting enzyme concentration the reaction rate can be controlled. The mechanical release rate of starch from gel can be controlled by changing the composition of starch gel, for example by casting a top gel with no starch or low starch concentration above the gel.

Figure 3A:
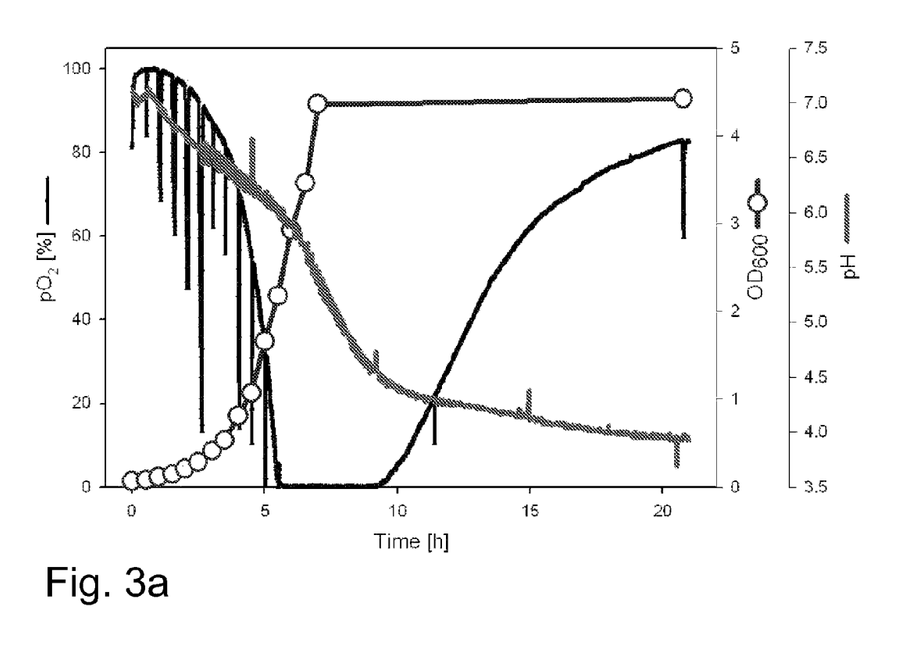
FIG. 3 shows that the described method works for controlling growth and providing high cell-densities in Escherichia coli shaken cultivation. The growth of bacteria was measured optically at 600 nm or 490 nm wavelength. A) Non-optimized shaken batch culture in mineral salt medium with 10 g/l initial glucose concentration. Non-controlled growth soon consumes all the oxygen. Accumulation of harmful metabolites stops the growth. B) Control of microbial growth obtained by the method of invention in shake flask cultivation. Glucose concentration became soon growth-limiting and high-cell densities were obtained. C) Cell yields and growth-speed in microtiter plate cultivations (100 µl liquid volumes). With correct enzyme dosing, high cell densities can be obtained.
Figure 3B:
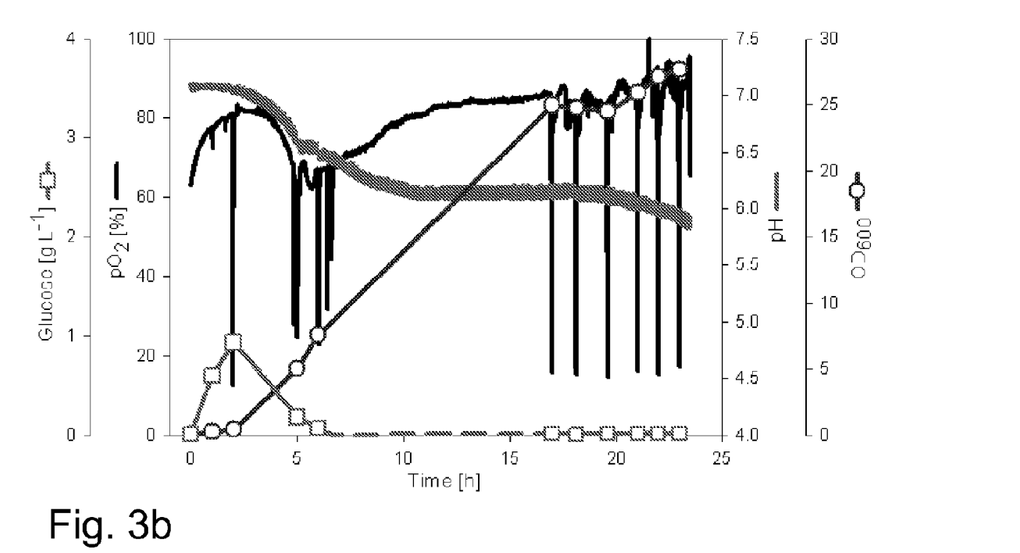
Figure 3C:
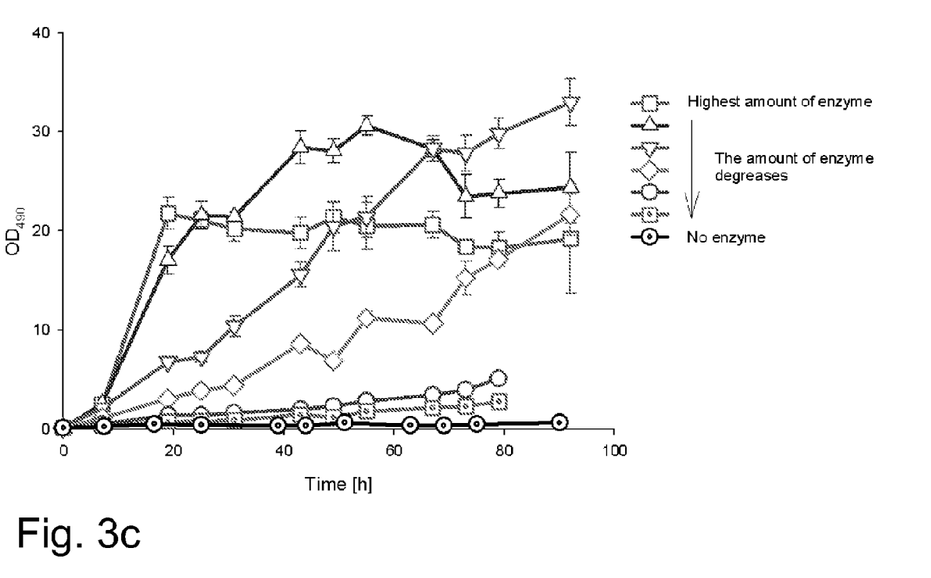

FIG. 3 shows that a typical batch-cultivation in a shake-flask (A) is characterized by non-controlled growth, oxygen depletion, accumulation of acidic metabolites and poor cell-yield (observed as a low $OD_{600}$). In contrast the method of the present invention (B) can provide glucose-limitation, slow but constant growth, prevent oxygen depletion and reduce the accumulation of metabolites that acidify the medium. FIG. 3C shows that a controlled growth can be obtained also in microtiter plate cultivations (100 µl liquid volume) by optimizing the enzyme dosing.

Figure 4:
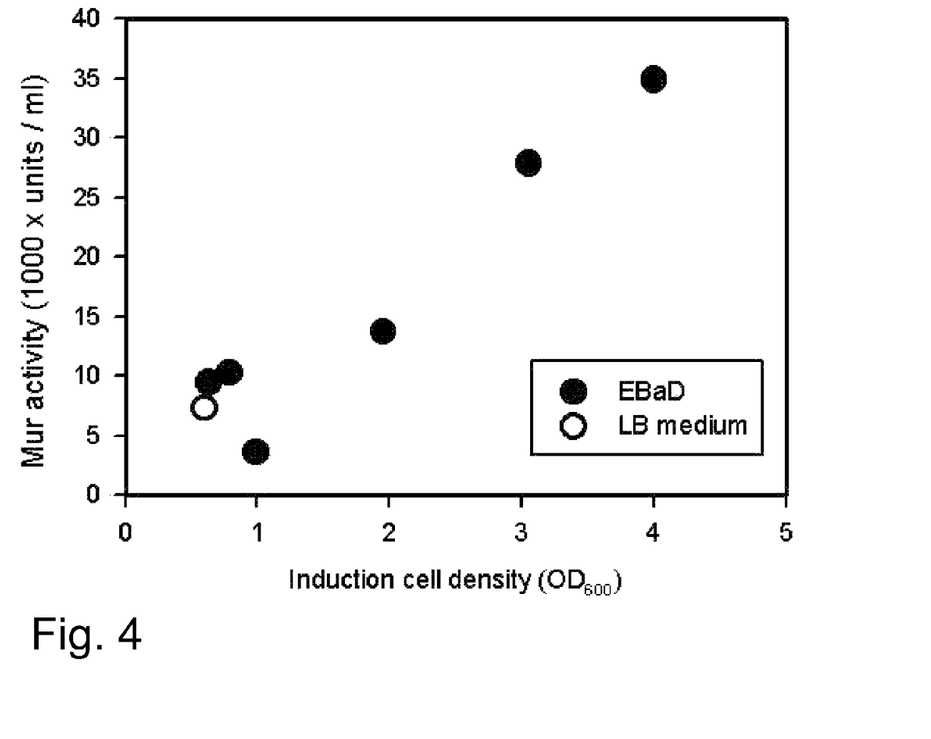
FIG. 4. shows the effect of the induction cell density on the yield of recombinant muramidase, produced in *E. coli* in deep-well plate cultivations (medium volume 0.7 ml, 2-layer starch-agar layer of 0.5 ml). Induction of the recombinant gene's expression was done with 0.5 mM IPTG. As a reference, induction of cultivation in LB medium (induction cell density $OD_{600}$=0.6) is shown. With the method of the present invention, considerably higher cell densities can be used than in normal protocols (induction cell densities ($OD_{600}$) from 0.2 to 0.6 are typically used).

Applicability of the method for inducible recombinant protein production was investigated with recombinant *E. coli* strain BL21(DE3)pET21c carrying the gene mur encoding *Lactobacillus* bacteriophage LL-H muramidase (lysozyme). Over-production of Mur is harmful for dividing cells because when leaked into periplasm it hydrolyzes the cell wall murein leading to cell lysis. Mur-activity can be easily quantified [Vasala A, Valkkila M, Caldentey J, Alatossava T: Genetic and biochemical characterization of the *Lactobacillus delbrueckii* subsp. *lactis* bacteriophage LL-H lysin. Appl Environ Microbiol 1995, 61: 4004-4011] and a high-cell-density fed-batch recombinant protein bioreactor process has been previously described [Viitanen M I, Vasala A, Neubauer P, Alatossava T: Cheese whey-induced high-cell-density production of recombinant proteins in *Escherichia coli*. Microb Cell Fact 2003, 2:2]. According to these studies Mur-production per cell mass can not be substantially improved. Therefore a successful production strategy is based on the use of a high induction cell density. A deep-well plate with 48 sample positions (2 ml volume) was used. The sample wells contained 0.6 ml of starch-agar gel (2-layer gel comprising 0.5 ml bottom gel and 0.1 ml upper gel) and 0.7 ml of the cultivation medium containing glucoamylase enzyme. Recombinant Mur production with various cell densities (FIG. 4) confirmed that the invented method is applicable for small-scale recombinant protein production in non-controlled cultivations. Bacteria cultivated with the method of the invention were induced at different cell-densities with 1 mM IPTG (inducer of gene mur), and 0.5 g/l glucose was added to ensure that carbon source will not limit the protein production. After 4 hours induction, a linear relationship between induction cell density and Mur-activity was obtained, when the induction cell density ($OD_{600}$) was higher than 0.9. Highest Mur-production was obtained with the highest induction cell density. As a reference system, a culture grown in Luria-Bertani (LB) medium and induced at $OD_{600}$ 0.6 was used, since higher induction cell densities in batch cultivation normally yield lower yield of recombinant proteins. This experiment confirmed that the method of invention is applicable for recombinant protein production in simple shaken cultures and allows the use of considerably higher cell densities compared to standard laboratory protocols.

This invention has been described with an emphasis upon some of the preferred embodiments and applications. However, it will be apparent for those skilled in the art that variations in the disclosed embodiments can be prepared and used and that the invention can be practiced otherwise than as specifically described herein within the scope of the following claims.

The invention claimed is:

1. A method for culturing an isolated microorganism in a fed-batch culture system, comprising:
    providing a two-phase fed-batch cultivation system in a cultivation vessel, the system comprising:
        (i) a liquid culture medium, and
        (ii) a gel-like matrix comprising at least one of agar-gel, carrageen-gel or gelatin-gel,
    wherein,
        the liquid culture medium initially comprises an initial amount of a nutrient substrate for the microorganism, and
        the gel-like matrix comprises a polymer substrate that cannot be utilized by the microorganism as a nutrient substrate but that can be enzymatically digested by an enzyme to form said nutrient substrate;
    inoculating the liquid culture medium with the microorganism and culturing the microorganism in said two-phase cultivation system in said cultivation vessel, wherein the microorganism utilizes the initial amount of nutrient substrate for growth;
    adding manually a desired amount of said enzyme to the liquid culture medium and allowing the enzyme to digest said polymer substrate, thereby forming the nutrient substrate,
        wherein the enzymatically formed nutrient substrate is then provided to the liquid culture medium, thereby providing more nutrient substrate to the liquid culture medium,
        and wherein the microorganism utilizes the enzymatically formed nutrient substrate for growth; and
    culturing the microorganism in said cultivation vessel to reach a desired final cell density.

2. The method of claim 1, wherein the polymer substrate is starch, the added enzyme is glucoamylase, and the enzymatically formed nutrient substrate is glucose, and wherein the starch is digested by the glucoamylase to form the glucose.

3. The method of claim 2, wherein the nutrient substrate is glucose and the initial amount of the glucose in the liquid culture medium is none.

4. The method of claim 2, wherein the gel-like matrix comprises 5% to 10% w/v starch and 5% to 7% w/v agar.

5. The method of claim 1, wherein the polymer substrate is digested by the enzyme in the gel-like matrix.

6. The method of claim 1, wherein the polymer substrate is distributed from the gel-like matrix into the liquid culture medium, and the polymer substrate is digested by the enzyme in the liquid culture medium.

7. The method of claim 1, wherein the gel-like matrix is present as a layer on the bottom of the cultivation vessel.

8. The method of claim 7, wherein the layer of gel-like matrix comprises an agar-gel.

9. The method of claim 7, wherein the cultivation system further comprises a second layer of gel overlaid on top of said layer on the bottom of the cultivation vessel, and the second layer is configured to control diffusion of the polymer substrate from the gel-like matrix to the liquid culture medium.

10. The method of claim 1, wherein the gel-like matrix comprises a bead matrix and is suspended in the liquid culture medium.

11. The method of claim 1, wherein the enzyme is amylase, protease, peptidase, nuclease or amidase.

12. A method for culturing an isolated microorganism in a fed-batch culture system, comprising:
providing a two-phase fed-batch cultivation system in a cultivation vessel, the system comprising:
(i) a liquid culture medium, and
(ii) a gel-like matrix comprising at least one of agar-gel, carrageen-gel or gelatin-gel,
wherein,
the liquid culture medium has an initial pH level, and
the gel-like matrix comprises a polymer substrate that can be enzymatically digested by an enzyme to release a pH adjusting agent;
inoculating the liquid culture medium with the microorganism and culturing the microorganism in said two-phase cultivation system in said cultivation vessel,
wherein during said culturing, the cultured microorganism produces acidic metabolites to, and/or consumes ammonium ions from, the liquid culture medium;
manually adding a desired amount of said enzyme to the liquid culture medium and allowing the enzyme to digest said polymer substrate, thereby forming said pH adjusting agent,
wherein the enzymatically formed pH adjusting agent is then provided to the liquid culture medium, thereby increasing the pH level of the liquid culture medium to a pH that is higher than the initial pH, or thereby maintaining the pH level of the liquid culture medium at a pH level that would otherwise drop due to the production of said acidic metabolites and/or the consumption of said ammonium ions by the cultured microorganism,
and wherein the growth and metabolic activity of the cultured microorganism in the cultivation vessel can be maintained by said increased or maintained pH level; and
culturing the microorganism in said cultivation vessel to reach a desired final cell density.

13. The method of claim 12, wherein the polymer substrate is digested by the enzyme in the gel-like matrix.

14. The method of claim 12, wherein the polymer substrate is distributed from the gel-like matrix into the liquid culture medium, and the polymer substrate is digested by the enzyme in the liquid culture medium.

15. The method of claim 12, wherein the gel-like matrix is present as a layer on the bottom of the cultivation vessel.

16. The method of claim 15, wherein the cultivation system further comprises a second layer of gel overlaid on top of said layer on the bottom of the cultivation vessel, and the second layer is configured to control diffusion of the polymer substrate from the gel-like matrix to the liquid culture medium.

17. The method of claim 12, wherein the layer of gel-like matrix comprises an agar matrix.

18. The method of claim 12, wherein the gel-like matrix comprises a bead matrix and is suspended in the liquid culture medium.

19. The method of claim 12, wherein the pH adjusting agent is ammonia.

* * * * *